(12) United States Patent
Choi

(10) Patent No.: US 12,364,211 B2
(45) Date of Patent: Jul. 22, 2025

(54) PLANT CULTIVATION APPARATUS

(71) Applicant: LG ELECTRONICS INC., Seoul (KR)

(72) Inventor: Minhwan Choi, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 0 days.

(21) Appl. No.: 18/269,116

(22) PCT Filed: Dec. 21, 2021

(86) PCT No.: PCT/KR2021/019520
§ 371 (c)(1),
(2) Date: Jun. 22, 2023

(87) PCT Pub. No.: WO2022/139415
PCT Pub. Date: Jun. 30, 2022

(65) Prior Publication Data
US 2024/0040973 A1    Feb. 8, 2024

(30) Foreign Application Priority Data

Dec. 22, 2020    (KR) .................. 10-2020-0181109

(51) Int. Cl.
*A01G 9/26* (2006.01)
*A01G 9/24* (2006.01)
*G05B 15/02* (2006.01)

(52) U.S. Cl.
CPC .............. *A01G 9/26* (2013.01); *A01G 9/246* (2013.01); *A01G 9/247* (2013.01); *A01G 9/249* (2019.05); *G05B 15/02* (2013.01)

(58) Field of Classification Search
CPC ........... A01G 9/26; A01G 9/249; A01G 31/06
See application file for complete search history.

(56) References Cited

U.S. PATENT DOCUMENTS

2021/0068358 A1\* 3/2021 Im ....................... G06V 20/00
2022/0192106 A1\* 6/2022 Kim ..................... A01G 31/06
(Continued)

FOREIGN PATENT DOCUMENTS

EP        3695706        8/2020
JP        4009441       11/2007
(Continued)

OTHER PUBLICATIONS

International Search Report dated Apr. 11, 2022 issued in Application No. PCT/KR2021/019520.
(Continued)

*Primary Examiner* — Kristen C Hayes
(74) *Attorney, Agent, or Firm* — KED & ASSOCIATES

(57) ABSTRACT

A plant cultivation apparatus is disclosed. The plant cultivation apparatus includes a cabinet, a bed, a cultivation unit, a photographing unit, and a control unit. The bed is provided inside of the cabinet. The cultivation unit is seated on the bed and accommodates a medium in which at least a portion of a plant is embedded. The photographing unit is provided inside of the cabinet and captures an image of the cultivation unit. The control unit is configured to receive a captured image from the photographing unit. The cultivation unit includes a cultivation container and a cover unit. The cultivation container is seated on the bed, is provided to have an open upper portion, and accommodates the medium therein. The cover unit shields the open tipper portion of the cultivation container and includes a cover through-hole provided at a position corresponding to the medium. The image captured by the photographing unit includes a first area including the cover through-hole, and a second area surrounding the first area. The control unit is configured to determine, through the image, an abnormal state of the plant according to a ratio of an area occupied by the plant in at least one of the first area or the second area.

20 Claims, 12 Drawing Sheets

(56) References Cited

U.S. PATENT DOCUMENTS

| | | | |
|---|---|---|---|
| 2022/0192118 A1* | 6/2022 | Yoo | A01G 31/06 |
| 2023/0095718 A1* | 3/2023 | Kuffner | A01G 9/247 47/65.9 |
| 2023/0255153 A1* | 8/2023 | Counne | A01G 27/003 47/17 |

FOREIGN PATENT DOCUMENTS

| | | |
|---|---|---|
| JP | 2013-094756 | 5/2013 |
| JP | 2018-073175 | 5/2018 |
| JP | 6330552 | 5/2018 |
| JP | 2019-128703 | 8/2019 |
| JP | 6752493 | 9/2020 |
| JP | 6782715 | 11/2020 |
| KR | 10-2017-0061293 | 6/2017 |
| KR | 10-2018-0062076 | 6/2018 |
| KR | 10-1869034 | 7/2018 |
| KR | 10-1954248 | 3/2019 |
| KR | 10-2020-0100499 | 8/2020 |
| KR | 10-2176107 | 11/2020 |
| TW | I714474 | 12/2020 |

OTHER PUBLICATIONS

European Search Report issued in Application No. 21911482.4 dated Oct. 18, 2024.

* cited by examiner

PLANT CULTIVATION APPARATUS

CROSS-REFERENCE TO RELATED PATENT APPLICATIONS

This application is a U.S. National Stage Application under 35 U.S.C. § 371 of PCT Application No. PCT/KR2021/019520, filed Dec. 21, 2021, which claims priority to Korean Patent Application No. 10-2020-0181109, filed Dec. 22, 2020, whose entire disclosures are hereby incorporated by reference.

TECHNICAL FIELD

A plant cultivation apparatus, and more particularly, a plant cultivation apparatus for determining an abnormal state of a plant through an image captured by a photographing portion is disclosed herein.

BACKGROUND ART

A plant cultivation apparatus refers to an apparatus capable of cultivating plants by artificially supplying light energy, moisture, soil, and temperature required for plant growth. The plant cultivation apparatus forms a predetermined cultivation space having an environment suitable for plant growth therein, and cultivates and stores plants in the predetermined cultivation space.

The plant cultivation apparatus may be provided with a configuration for supplying moisture and nutrients required for plant growth. In addition, plants cultivated in the plant cultivation apparatus may receive light energy artificially from the plant cultivation apparatus without receiving light irradiated from the sun outside of the plant cultivation apparatus.

As a result, the user may cultivate plants by supplying water or nutrients periodically during the plant cultivation process, and the plants cultivated in the plant cultivation apparatus can grow by receiving nutrients, moisture, and light energy supplied from the plant cultivation apparatus.

A photographing device may be installed in the plant cultivation apparatus to provide the user with growth information of the plant inside. As the user can receive growth information of plants cultivated in the cultivation space in the plant cultivation apparatus through the photographing device without visually checking the plant, user convenience and reliability of the plant cultivation apparatus can be improved.

However, conventional plant cultivation apparatus deliver simple visual information about plants cultivated in a cultivation space to the user through a photographing device, but the visual data obtained by the photographing device cannot be used to control plant cultivation, for example.

Further, as a method for obtaining plant development status information, there was a plant cultivation apparatus with an artificial intelligence (AI) function using deep learning, but the method for obtaining plant development status information through deep learning is inefficient in terms of cost and time because it is inevitable to acquire a lot of data to improve accuracy. Furthermore, as a control device for obtaining plant development state information through deep learning is configured, there is a problem of inefficiency in terms of cost. Therefore, it is an important task in the art to design a plant cultivation apparatus in which a photographing device photographs the developmental state of a plant and identifies an abnormal state of the plant through simple image analysis of the photographed image. In addition, it is an important task in the art to design a plant cultivation apparatus that identifies the abnormal state of a plant and restores the abnormal state of the plant to a normal state.

DISCLOSURE

Technical Problem

Embodiments provide a plant cultivation apparatus capable of easily identifying the state of plants cultivated in the cultivation portion through the photographing unit by providing a photographing portion inside of the cabinet for photographing the cultivation portion.

Embodiments further provide a plant cultivation apparatus capable of determining an abnormal state of a plant cultivated in a cultivation portion by analyzing an image photographed by a photographing portion.

Embodiments furthermore provide a plant cultivation apparatus that can efficiently determine the abnormal state of a plant in terms of cost and time by analyzing data acquired by the photographing portion.

Embodiments also provide a plant cultivation apparatus that analyzes the abnormal state of a plant through an image photographed by a photographing portion and induces recovery from an abnormal state to a normal state.

Technical Solution

Embodiments provide a plant cultivation apparatus including a cabinet, a bed, a cultivation portion, a photographing portion, and a controller in order to solve the above problems. More specifically, the bed is provided inside of the cabinet, at least a portion of the plant accommodates a medium in which at least a portion of the plant is embedded, the photographing portion is provided inside of the cabinet, and photographs the cultivation portion, and the controller is provided to receive the photographed image from the photographing portion. The cultivation portion includes a cultivation container and a cover portion, the cultivation container is seated on the bed and provided with an open top, the medium is accommodated therein, and the cover portion shields the open upper portion of the cultivation container, and a cover through-hole provided at a position corresponding to the medium.

The image of the photographing portion includes a first region including the cover through-hole and a second region surrounding the first region. The controller is provided or configured to determine an abnormal state of the plant according to a region ratio occupied by the plant in at least one of the first region and the second region through the image.

In the plant cultivation apparatus according to an embodiment, the controller may be provided to perform a first position determination mode for defining the first region by using a color difference between the cover portion and the cover through-hole in the image. The controller may be provided or configured to define a second region extending in a radial direction from the first region by a predetermined distance in the first position determination mode.

The cover portion may include a display portion or display that determines a relative position with respect to the cover through-hole. The image of the photographing portion may include the display portion. The controller may be provided or configured to perform a second position determination mode for defining the first region by identifying a position of the display portion in the image and reflecting the relative position.

The controller may be provided or configured to perform a germination determination mode for determining whether the plant has germinated based on a region ratio occupied by the plant in at least one of the first region and the second region. In addition, the controller may identify the region ratio occupied by the plant in at least one of the first region or the second region through a color difference between the cover portion, the cover through-hole, and the plant identified in the image in the germination determination mode.

The controller may be provided or configured to perform a hardness determination mode for determining whether the plant has fallen through a region ratio occupied by the plant in at least one of the first region or the second region. In addition, the controller may be provided or configured to determine that the plant is in a fallen state when the region ratio occupied by the plant in the first region is equal to or less than the first region ratio and the region ratio occupied by the plant in the second region is equal to or greater than the second region ratio.

The second region may be divided into a plurality of zones along a circumference of the first region. The controller may be provided or configured to determine a falling direction of the plant by identifying a region ratio occupied by the plant for each of the plurality of zones.

A cultivation space in which the plant is cultivated may be formed inside of the cabinet. The plant cultivation apparatus according to an embodiment may further include a blower including a blower fan provided in the cabinet to circulate air in the cultivation space.

The controller may be provided to perform a blowing mode for adjusting an amount of air circulation in the cultivation space by controlling the blower when the fallen state of the plant is determined in the hardness determination mode. The blowing mode may include a first blowing mode, and the controller may be provided to reduce a rotational speed of the blowing fan in the first blowing mode to induce the prevention of falling of the plant.

The blowing mode may include a second blowing mode. The controller may be provided to increase a quality of the image photographed by the photographing portion by stopping operation of the blower fan in the second blowing mode.

The plant cultivation apparatus according to an embodiment may further include a light emitting portion including a light emitting body provided inside of the cabinet and that irradiates light toward the cultivation portion. When the controller determines that the plant is in the fallen state in the hardness determination mode, the controller controls the light emitting portion to increase a light amount of the light emitting body so that a first light amount adjustment mode for inducing recovery of the plant in the fallen state may be performed.

The controller may be provided or configured to perform a growth abnormality determination mode for determining whether the plant is in a growth abnormality state by identifying a color of the plant in the image of the photographing portion. The image of the photographing portion may include a third region corresponding to a region other than the first region and the second region of the upper surface of the cover portion. The controller may be provided or configured to determine that the plant is in a growth abnormality state when the growth abnormality color is identified from the plant in the second region and the third region in the growth abnormality determination mode.

When the plant is determined to be in the growth abnormality state in the growth abnormality determination mode, the controller may control the light emitting portion to reduce the light amount of the light emitting body so that a second light amount adjustment mode inducing recovery of the plant in the growth abnormality state may be performed.

In addition, the plant cultivation apparatus according to an embodiment may further include a water supply portion provided inside of the cabinet and that supplies nutrient solution to the cultivation portion. The controller may perform a flow rate adjustment mode for adjusting the nutrient solution supplied to the cultivation portion by controlling the water supply portion when the controller determines that the plant is in the growth abnormality state in the growth abnormality determination mode.

Each feature of the above-described embodiments may be implemented in combination in other embodiments unless inconsistent with or exclusive of the other embodiments.

Advantageous Effect

Embodiments may provide a plant cultivation apparatus that includes a photographing portion inside of the cabinet to photograph the cultivation portion and may easily identify a state of plants cultivated in the cultivation portion through the photographing portion.

Embodiments may further provide a plant cultivation apparatus capable of determining an abnormal state of a plant cultivated in a cultivation portion by analyzing an image captured by a photographing portion.

Embodiments may furthermore provide a plant cultivation apparatus that may efficiently determine the abnormal state of a plant in terms of cost and time by analyzing the data acquired by the photographing portion.

Embodiments provide a plant cultivation apparatus that analyzes an abnormal state of a plant through an image photographed by a photographing portion and induces recovery from an abnormal state to a normal state.

Effects of the embodiments are not limited to those described above, and other effects not mentioned can be clearly recognized by those skilled in the art from the description below.

BEST MODE

Figure 1:
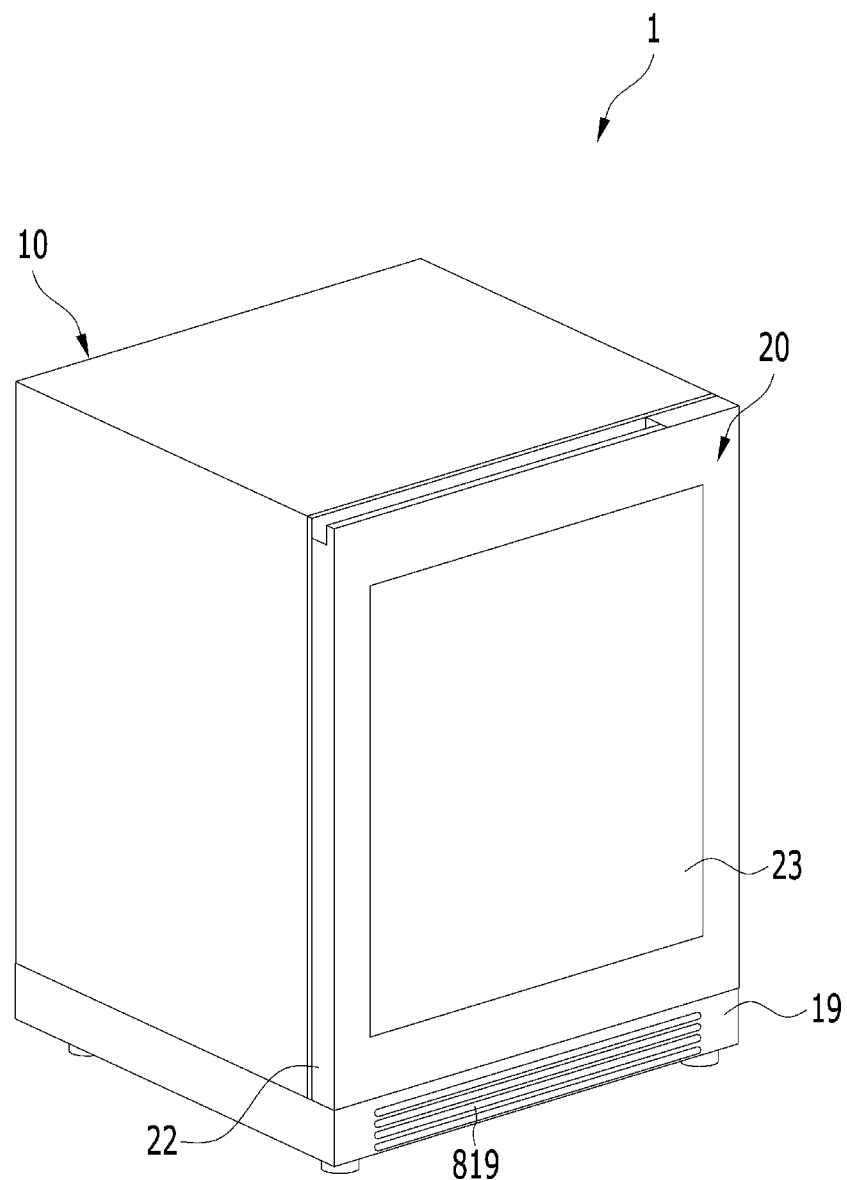
FIG. 1 is a perspective view illustrating a plant cultivation apparatus according to an embodiment.

Hereinafter, embodiments disclosed in this specification will be described with reference to the accompanying drawings. In this specification, the same or similar reference numerals are given to the same or similar components even in different embodiments, and the description is replaced with the first description. Singular expressions used herein include plural expressions unless the context clearly dictates otherwise. In addition, in describing the embodiments disclosed in this specification, if it is determined that a detailed description of related known technologies may obscure the subject matter of the embodiment disclosed in this specification, the description thereof will be omitted. In addition, it should be noted that the accompanying drawings are only for easy understanding of the embodiments disclosed in this specification, and should not be construed as limiting the technical idea disclosed in this specification by the accompanying drawings.

In addition, terms to be described hereinafter are terms defined in consideration of functions, which may vary according to the intention or custom of a user or operator. Therefore, the definition should be made based on the contents throughout this specification. Terminology used in the detailed description is only for describing the embodiments and should in no way be limiting. In this description, expressions such as "comprising" or "providing" are intended to indicate any characteristic, number, step, operation, element, portion or combination thereof, and it should not be interpreted to exclude the existence or possibility of one or more other characteristics, numbers, steps, operations, elements, portions or combinations thereof other than those described.

In addition, in describing the components of the embodiments, terms such as first, second, A, B, (a), and (b) may be used. These terms are only used to distinguish the component from other components, and the nature, sequence, or order of the corresponding component is not limited by the term.

Figure 2:
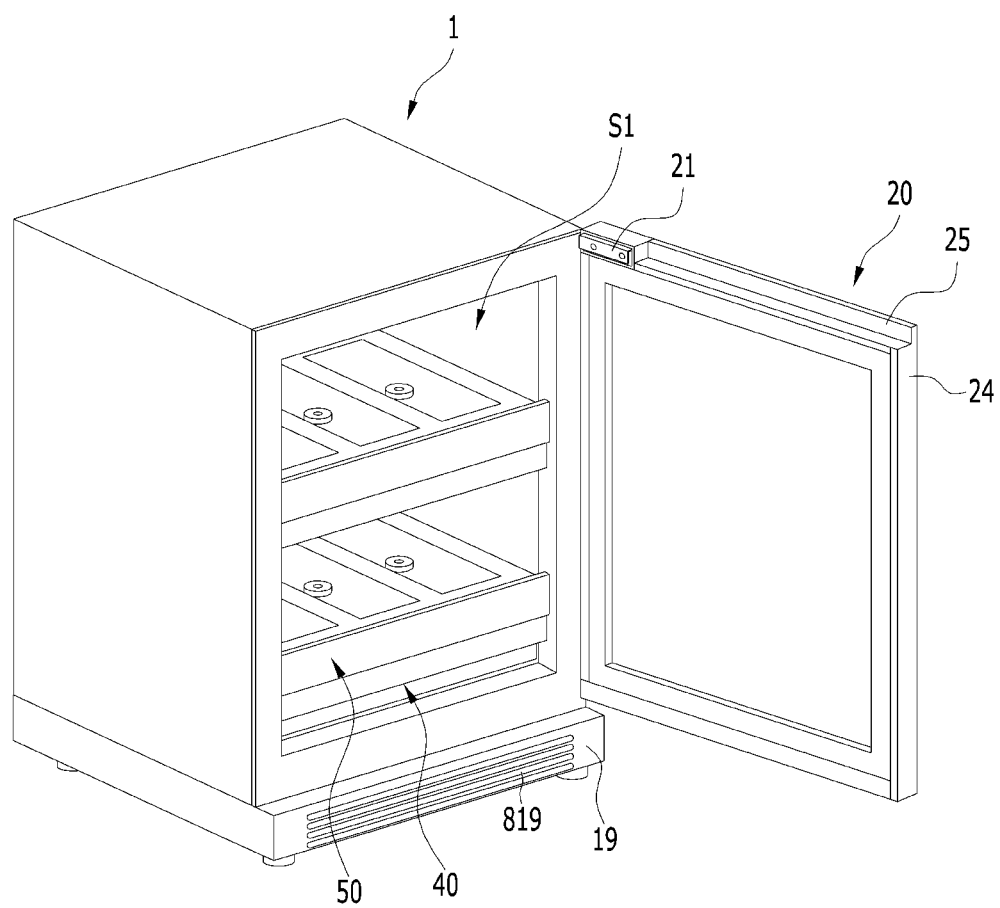
FIG. 2 is a perspective view illustrating a state in which a door is open in the plant cultivation apparatus according to an embodiment.

FIG. 1 is a perspective view illustrating a plant cultivation apparatus according to an embodiment. FIG. 2 is a perspective view illustrating a state in which a door is open in the plant cultivation apparatus according to an embodiment.

As illustrated in FIGS. 1 and 2, an outer appearance of plant cultivation apparatus 1 according to an embodiment may be formed by a cabinet 10 forming a cultivation space S1 in which plants are cultivated, and a door 20 that opens and closes the cabinet 10. The plants cultivated in the cultivation space S1 may correspond to types that are edible, easy to cultivate, and do not take up much space, such as leafy vegetables and herbs that can be commonly used for wraps or salads.

One side of the cabinet 10 is open, an opening may be formed on the one side thereof, and the cultivation space S1 may be formed therein. The cabinet 10 may be formed in a rectangular parallelepiped as illustrated in the drawing; however, embodiments are not necessarily limited thereto, and may be formed in various shapes, such as a cylinder or a sphere, as long as the cultivation space S1 may be formed therein.

As illustrated in FIGS. 1 and 2, the door 20 may be formed in a size capable of shielding an open side of the cabinet 10. Hereinafter, for convenience of explanation, the direction in which the opening faces is described as a forward direction.

The door 20 may have a door panel portion (door panel) 23 at least partially transparent. The door panel portion 23 may be formed of glass or a transparent plastic material, for example, to have a structure capable of seeing through to the inside. As the door panel portion 23 is provided in front of the door 20, the user may visually check the inside of the cultivation space S1 even in a state in which the door 20 is closed, and may check a growth state of the plants cultivated in the cultivation space S1.

In addition, the door panel portion 23 may have a color or a colored coating, metal deposition, or a film may be attached thereto, for example, and the cultivation space S1 may be selectively visible with the naked eye from the outside.

The door 20 may include a door frame 22 that forms a circumference and having a central portion open to form the opening. The door panel portion 23 may be configured to shield the opening of the door frame 22.

In addition, the door 20 may include a door sealing member 24 provided on a surface of the door frame 22 facing the cabinet 10 and disposed along a circumference of the opening of the door frame 22. When the door 20 is closed, the door sealing member 24 may contact the cabinet 10 and shield the cultivation space S1. The door sealing member 24 may absorb an impact force applied to the cabinet 10 by the door 20 when the door 20 is closed, thereby improving durability and reliability of the plant cultivation apparatus.

In addition, the door sealing member 24 blocks the flow of air outside of the cultivation space S1 and the cabinet 10, so that the temperature and humidity of the cultivation space S1 may be maintained constant. In addition, as the door sealing portion 24 may be formed of an insulation material, the cabinet 10 may be insulated, and thus, the cultivation space S1 may maintain a temperature set by the user.

The door 20 may be provided with a door coupling portion 21 provided on one side of the door frame 22 and coupled with the cabinet 10. As illustrated in FIGS. 1 and 2, a door coupling portion 21 may be provided on one or a first side of both sides of the door frame 22 in a lateral or a leftward and rightward direction. Accordingly, the door may be opened and closed on the one side of both sides based on the user in the leftward and rightward direction, so that the user's convenience may be increased.

In addition, the door 20 may be rotatably coupled to the cabinet 10 through the door coupling portion 21. The cultivation space S1 may be opened and closed according to rotation of the door 20.

The door 20 may be provided at one end of an upper end or a lower end of the door frame 22 and may include a door handle 25 for a user to open and close the door 20. When the door coupling portion 21 is provided on the one side of both sides of the door frame 22 in the leftward and rightward direction, the door handle 25 may be provided on the other or a second side of both sides of the door frame 22 in the leftward and rightward direction.

A lower cabinet 19 may be disposed under the cabinet 10. A blower 80 may be provided in the cabinet 10 to introduce outside air and supply the outside air to the cultivation space S1.

Figure 3:
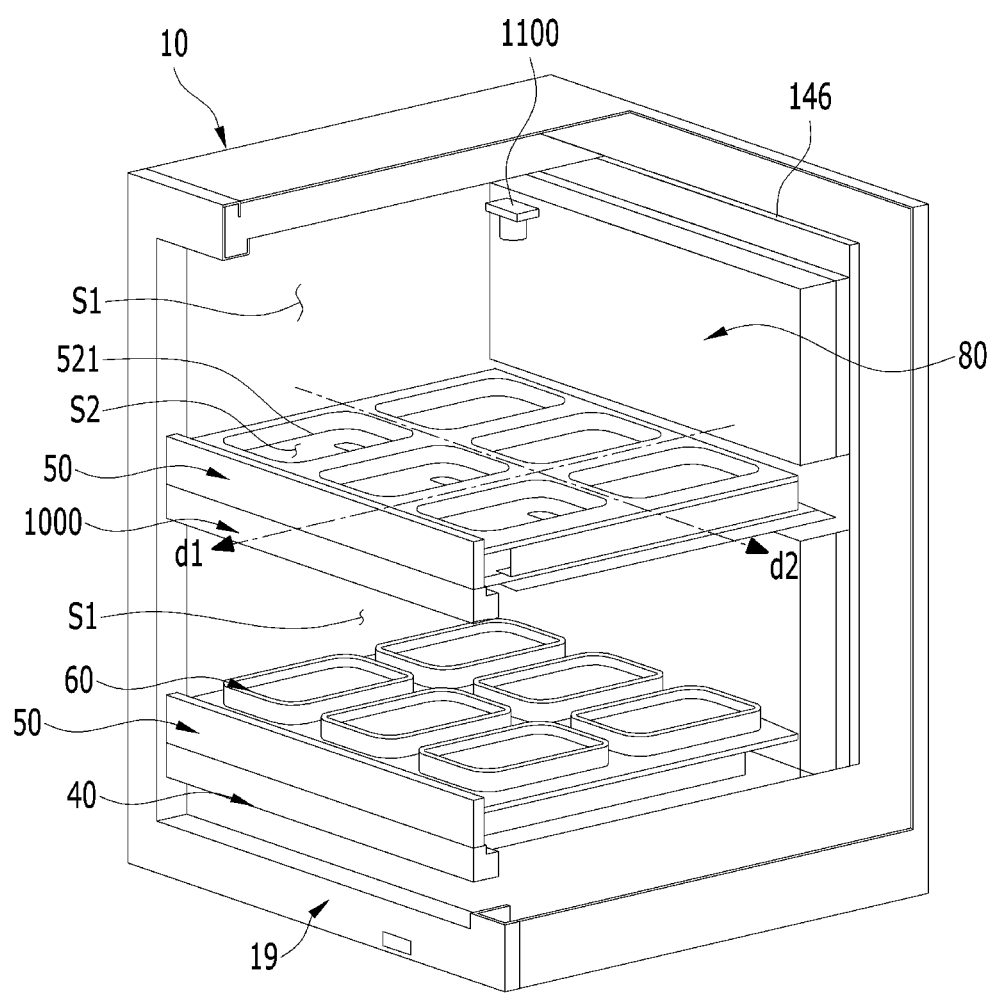
FIG. 3 is a perspective view illustrating an inside of a cabinet provided with a photographing portion in the plant cultivation apparatus according to an embodiment.

FIG. 3 is a perspective view illustrating the inside of a cabinet provided with a photographing portion in the plant cultivation apparatus according to an embodiment. FIG. 3 illustrates bed 50, cultivation portion 60, and photographing portion 1100 provided inside of the cabinet 10 in the plant cultivation apparatus 1 according to an embodiment.

In the plant cultivation apparatus 1 according to an embodiment, a plurality of beds 50 may be disposed vertically inside of the cabinet 10. In addition, as illustrated in FIG. 3, in the plant cultivation apparatus 1 according to an embodiment, two beds 50 may be provided at upper and lower portions inside of the cabinet 10 based on a front side where the door 20 is provided.

Hereinafter, for convenience of explanation and understanding, the two beds 50 may be referred to as upper bed 50 and lower bed 50, respectively. Of course, a plurality of beds 50, such as the three or more beds, may be provided according to a size of the cabinet 10.

In addition, a plurality of cultivation portions 60 containing plant seeds and nutrients necessary for cultivation may be seated on an upper portion of the bed 50. The bed 50 may be referred to as a shelf or a tray and may form a cultivation space S1 in which the cabinet 10 and plants are cultivated inside of the cabinet 10.

The bed 50 may be provided inside of the cabinet 10 so as to be drawn in and out of the cabinet 10 through the door 20. When the user places the cultivation portion 60 on the upper portion of the bed 50 or separates the cultivation portion 60 from the bed 50, the bed 50 may be exposed to the outside of the cabinet 10, so user convenience may be increased.

In addition, as will be described hereinafter, the bed 50 may be provided with a discharge flow path portion 512 through which water supplied from a water supply portion (water supply) 40 moves, and the discharge flow path portion 512 may be configured to supply a nutrient solution necessary for plants to the cultivation portion 60 from the water supply portion 40 at all times. The water supply portion 40 may include a water supply case 42 having a storage portion (not illustrated), a supply pump portion (not illustrated), and a branch valve (not illustrated) described hereinafter. The storage portion (not illustrated) may supply water required by the plant to the cultivation portion 60, store water required for the plant, and store water recovered from the cultivation portion 60.

The cultivation portion 60 may be provided in a form in which various types of seeds and suitable nutrients are suitably combined, and the user may select a product desired for cultivation. In addition, the bed 50 may have a structure in which the cultivation portion 60 may be seated and maintained in a seated state.

Medium 64 embedded in the cultivation portion 60 may contain plant seeds. The plant's roots may pass through the medium 64 to receive nutrient solution.

The cultivation portion 60 may be seated on the bed 50 so that nutrient solution (hereinafter, water) may be supplied from the water supply portion 40 through the discharge flow path portion 512 described hereinafter and may be provided so that the water is discharged through the discharge flow path portion 512 to the storage portion (not illustrated).

A plurality of cultivation portions 60 may be provided on the bed 50, and various types of plants may be cultivated in one of the plurality of cultivation portions 60. In other words, the cultivation portion 60 may be provided in a form in which various types of seeds and suitable nutrients are suitably combined, and the user may select a plant to be cultivated and grow the desired plant on the cultivation portion 60.

The cultivation portion 60 may be seated on the bed 50 so that the cultivation portion 60 may be separated from the bed 50. Thus, the user may accommodate the medium 64 containing the seeds of the plant from outside of the plant cultivation apparatus 1 in the cultivation portion 60, and may seat the cultivation portion 60 on the bed 50 at one side where the cabinet 10 is open.

When the plant grows and harvest time arrives, the user may separate the cultivation portion 60 from the bed 50, and the plant of the cultivation portion 60 may be easily harvested from outside of the plant cultivation apparatus 1, so that the user may increase ease and convenience of harvesting.

The cultivation portion 60 may be formed in a shape extending from one or a first side to the other or a second side. A direction in which the cultivation portion 60 extends may be a direction d1 toward the door 20 from the cultivation space S1. In some cases, the direction in which the cultivation portion 60 extends may be formed in any direction on the bed 50.

As illustrated, the plurality of cultivation portions 60 may be spaced apart from each other and seated on the upper portion of the bed 50 based on the extending direction d1 and an inclined direction d2 of the cultivation portion 60. Hereinafter, for convenience of description, a direction in which the cultivation portion 60 extends is defined as "first direction d1", and a direction inclined from the first direction d1 is defined as "second direction d2".

The first direction d1 may be a forward direction from the cultivation space S1 toward the door 20. The second direction d2 may be a lateral direction in which sides of the cabinet 10 face each other.

The bed 50 may be formed in the shape of a rectangular plate, for example, that partitions the cabinet 10. Although not illustrated in the drawing, as described above, the bed may be seated on draw-in and out guides (not illustrated) mounted on both sides of an inside of the cabinet 10 so as to be drawn in and out.

As will be described hereinafter, a bed water collection portion 524 configured to receive water through the water supply portion 40 may be formed on or at one side of the bed 50. The bed water collection portion 524 is connected to the discharge flow path portion 512 provided inside of the bed 50 so that the water supplied to the bed water collection portion 524 may be continuously supplied to the cultivation portion 60.

The plant cultivation apparatus 1 according to an embodiment includes photographing portion 1100 provided inside of the cabinet 10 to photograph the cultivation portion 60. The photographing portion 1100 may correspond to a camera capable of obtaining visual information by photographing the cultivation portion 60 or the bed 50. The photographing portion 1100 may generate an image of the cultivation portion 60 or the bed 50 by acquiring light reflected from the bed 50. The photographing portion 1100 may correspond to various visual information acquisition devices capable of acquiring visual images of the cultivation portion 60 or the bed 50, as well as a camera.

A display portion (display) 1000 may be provided in the open opening of the cabinet 10. The display portion 1000 may output an operation state of the plant cultivation apparatus 1 to the outside. The display portion 1000 may include a manipulation portion (not illustrated) through which a user inputs a manipulation, and the user executes an input manipulation through the manipulation portion (not illustrated) and may set and input an overall operation of the plant cultivation apparatus 1 through the display portion 1000. The display portion 1000 may include, for example, a touch screen structure and may include structures, such as buttons and switches.

Figure 4:
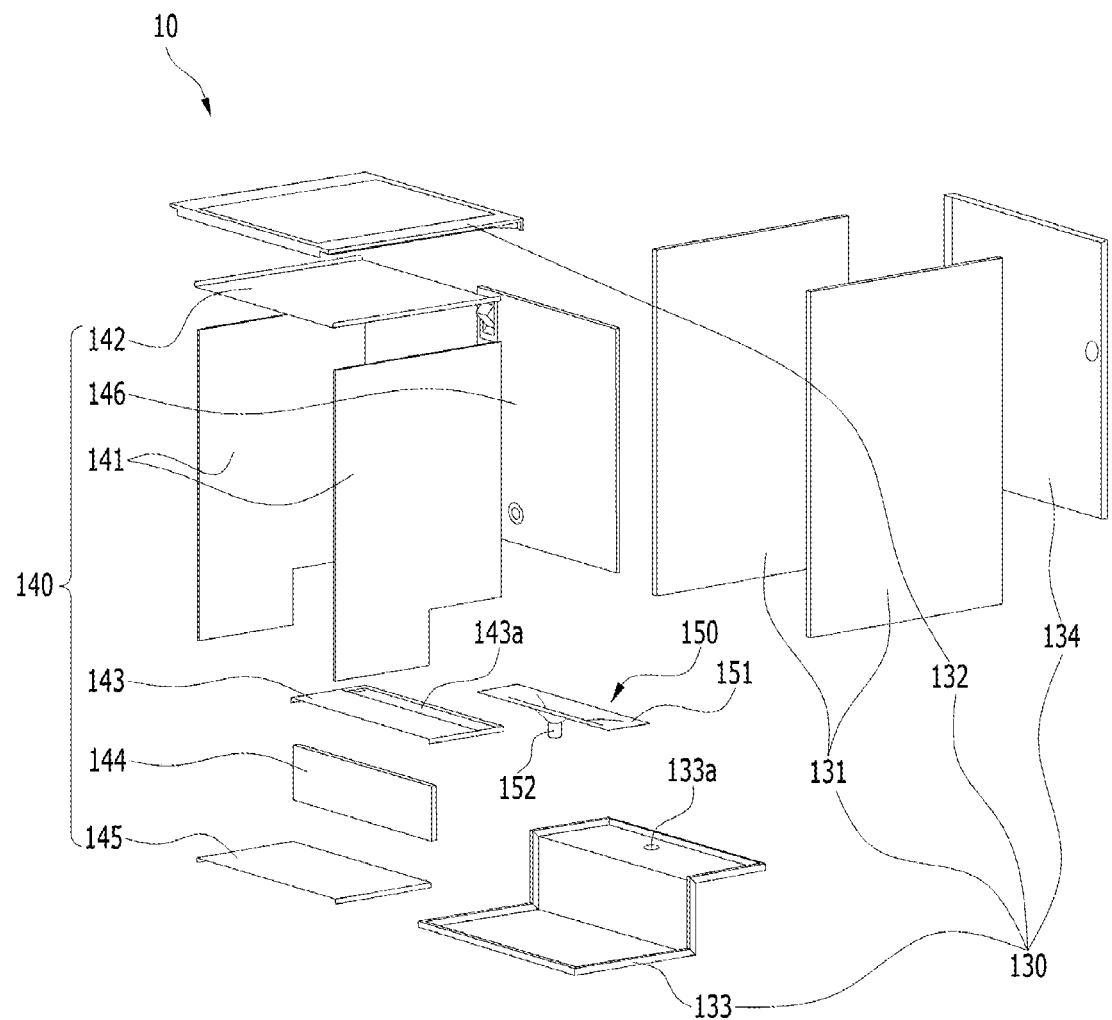
FIG. 4 is an exploded view illustrating a cabinet in a plant cultivation apparatus according to an embodiment.
Figure 5:
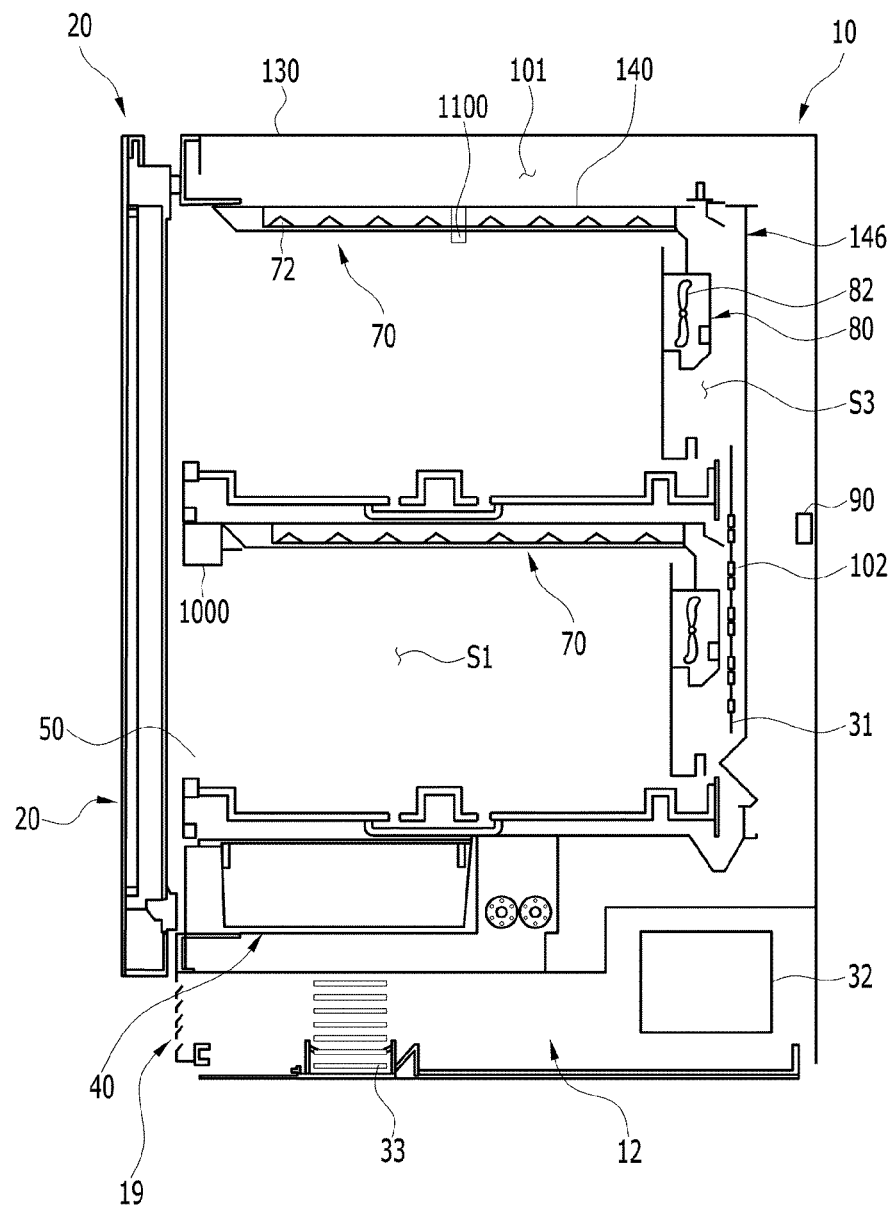
FIG. 5 is a side view illustrating the inside of the cabinet in the plant cultivation apparatus according to an embodiment.

FIG. 4 is an exploded view illustrating a cabinet in a plant cultivation apparatus according to an embodiment. FIG. 5 is a side view illustrating the inside of the cabinet in the plant cultivation apparatus according to an embodiment.

As illustrated in FIG. 4, the cabinet 10 may include an outer case 130 forming an outer shape and an inner case 140 forming the cultivation space S1. In addition, an insulation material 101 may be provided between the outer case 130 and the inner case 140, so that the plant cultivation apparatus 1 according to an embodiment may insulate the cultivation space S1 inside of the cabinet 10 from the outside of the cabinet 10 via the insulation material 101.

The outer case 130 may be formed of, for example, a metal material and may be composed of, for example, one or more plates forming an outer surface of the cabinet 10. In addition, the outer case 130 may include a pair of outer side plates 131 forming both sides of the outer surface of the cabinet 10 in the lateral or leftward and rightward direction, and an outer upper plate 132 forming an upper surface of the outer surface of the cabinet 10, an outer rear plate 134 forming a rear surface of the outer surface of the cabinet 10, and an outer lower plate 133 forming a lower surface of the outer surface of the cabinet 10.

The outer lower plate 133 may be bent so that a machine room 12 may be provided at a rear lower portion of the cabinet 10. As will be described hereinafter, the machine room 12 may include a compressor 32, and a condenser 33, for example, and the machine room 12 may be configured as a separate space partitioned from the cultivation space S1.

As illustrated in FIG. 5, a controller 90 may be provided on a rear surface of the cabinet 10, that is, on a rear surface of the outer rear plate 134. The controller 90 may be configured to control the entire operation of the plant cultivation device. The controller 90 may include a compressor printed circuit board (PCB) (not illustrated) provided separately to control the compressor 32. In addition, as will be described hereinafter, the controller 90 may be configured to receive an image photographed by the photographing portion 1100.

The plant cultivation apparatus 1 according to an embodiment may include a light emitting portion 70 including a light emitting body 72 provided in the cabinet 10 and that irradiates light toward the cultivation space S1. The light emitting portion 70 may be provided above the bed 50, and may provide light necessary for plants by irradiating light toward the bed 50. An amount of light irradiated by the light emitting portion 70 may be set to be similar to sunlight, and the amount of light and irradiation time optimized for the plant to be cultivated may be set.

When the light emitting portion 70 is turned on in a state in which the door 20 is closed, the inside of the cultivation space S1 becomes bright, and the inside thereof may be seen through the door panel portion 23. In addition, when the power supply to the light emitting portion 70 is cut off in a state in which the door 20 is closed, the inside of the cultivation space S1 becomes dark, and the cultivation space S1 may be made invisible by color or optical characteristics of the door panel 23.

The inner case 140 may be composed of, for example, a plurality of plates forming the cultivation space S1 inside of the cabinet 10. At least a portion of the inner case 140 may be formed of a plastic material, for example. In addition, the inner case 140 may be formed of, for example, a metal material having excellent thermal conductivity, such as aluminum. The metal inner case 140 has excellent heat transfer performance, so that the cultivation space S1 may have a uniform temperature distribution when heating or cooling the cultivation space S1.

The inner case 140 may be configured to reflect light irradiated from the light emitting portion 70. The light irradiated from the light emitting portion 70 may be reflected from a surface of the inner case 140 made of a metal material so that the light may be evenly irradiated to the plants in an entire region of the bed 50, and a shade region where the light is not irradiated may be cleared. To this end, each surface of the inner case 140 may be further subjected to surface treatment, painting, or film attachment to improve reflective performance. The inner case 140 may include an inner side plate 141 forming both side surfaces of the inner case 140, an inner upper plate 142 forming an upper surface of the inner case 140, an inner rear plate 146 forming a rear surface of the inner case 140, and inner lower plates 143, 144, and 145 forming a lower surface of the inner case 140.

The evaporator 31 may be disposed on a front surface of the inner lower plate 146, and a heater 102 may be provided on a rear surface of the inner lower plate 146. Therefore, heating and cooling of the air introduced into the cultivation space S1 from the rear of the cultivation space S1 may be performed.

The plant cultivation apparatus 1 according to an embodiment may include a blower 80 including a blower fan 82 provided in the cabinet 10 to circulate air in the cultivation space S1.

The evaporator 31 may be positioned between the inner lower plate 146 and the blower 80 and may be cooled by refrigerant flowing by driving the compressor 32. In addition, air cooled from the evaporator 31 circulates inside of the cultivation space S1 through the blower 80 to evenly cool the cultivation space S1.

The heater 102 may be provided on a rear surface of the inner lower plate 146 and may be configured to be buried in the insulation material 101. The heater 102 may be disposed in a region corresponding to the evaporator 31. The air heated by operation of the heater 102 is introduced into the cultivation space S1 through the blower 80 and may be circulated in the cultivation space S1. In addition, as the heater 102 is located in a region corresponding to the evaporator 31, the heater 102 may be operated when the evaporator 31 freezes and may be used for defrosting the evaporator 31.

By the evaporator 31 and the heater 102, the inside of the cultivation space S1 may be maintained at a temperature suitable for plant growth. Although not illustrated in the drawings, the plant cultivation apparatus 1 according to an embodiment may include a temperature sensor (not illustrated) provided in the cabinet 10 to measure a temperature in the cultivation space S1. The temperature of the cultivation space S1 may be maintained constant regardless of an external temperature of the cabinet 10 through the temperature sensor (not illustrated).

The inner lower plates 143, 144, and 145 may be formed in a shape corresponding to a bent shape of the outer lower plate 133, and may be formed by the first lower plate 143, the second lower plate 144, and the third lower plate 145, respectively. The first lower plate 143, the second lower plate 144, and the third lower plate 145 may be coupled to each other.

A return duct hole 143a to which a return duct 150 is mounted may be formed in the first lower plate 143. The return duct 150 may have a structure communicating with the machine room 12 to discharge air inside of the cultivation space S1 to the machine room 12.

The return duct 150 may be composed of a duct mounting portion 151 mounted in the return duct hole 143a and a duct discharge pipe that extends inwardly toward the machine room 12 through opening 133a of the outer lower plate 133 at a center of the duct mounting portion 151. The duct mounting portion 151 may be disposed at a lower portion of the inner lower plate 146 and a lower portion of the evaporator 31, and when condensation occurs in the evaporator 31, may be formed so that water is discharged to the machine room 12. In addition, a drain pan (not illustrated) capable of collecting water discharged through the return duct 150 may be provided inside of the machine room 12.

The machine room 12 may include a supply duct (not illustrated) that communicates with an air flow space S3 formed between the blower 80 and the inner rear plate 146, and carbon dioxide ($CO_2$) required for plant growth may be supplied from the machine room 12 to the air flow space S3 through the supply duct (not illustrated).

In other words, the air in the cultivation space S1 may be discharged to the air flow space S3 through the blower 80, and discharged from the air flow space S3 through the return duct 150. The inside of at least one of the supply duct (not illustrated) or the return duct 150 may be configured to be opened and closed so that at least one of the supply duct (not illustrated) or the return duct 150 may be opened when carbon dioxide is supplied to the cultivation space S1.

The photographing portion 1100 is provided inside of the cabinet 10 to photograph the cultivation portion 60. The photographing portion 1100 may be configured to transmit a visual image to the controller 90 by photographing the cultivation portion 60 or the bed 50, and may correspond to, for example, a camera.

As illustrated in FIG. 5, the photographing portion 1100 may pass through the light emitting portion 70 and be coupled to the cabinet 10, and may be coupled to an inner surface of door frame 22 to photograph the cultivation portion 60 or the bed 50. Hereinafter, for convenience of description, as illustrated in FIG. 5, the photographing portion 1100 will be described as being provided above the cultivation portion 60.

The photographing portion 1100 may be provided at a position corresponding to a center of one surface of the bed 50 facing the light emitting portion 70, and may be configured to photograph all of the plurality of cultivation portions 60. The photographing portion 1100 may be configured to transmit a photographed image to the controller 90, and may be configured to photograph the cultivation portion 60 upon receiving a photographing command from the controller 90. The photographing portion 1100 may be configured to capture an image of the cultivation portion 60 even in a state in which there is no light in the cultivation space S1, but for convenience of explanation, it will be described that the photographing portion 1100 photographs in a state in which there is light in the cultivation space S1.

The plant cultivation apparatus 1 according to an embodiment may include the blower 80 including the blower fan 82 provided in the cabinet 10 to circulate air in the cultivation space S1. The blower 80 may be provided in front of the evaporator 31 and may be provided in each of the cultivation spaces S1 divided by the bed 50.

The plurality of blowers 80 disposed in one direction in which the cultivation space S1 is arranged may have a same structure and shape, except for differences in mounting positions. In addition, the blower 80 may be provided in a number corresponding to the number of beds 50, and may blow air from a rear of the bed 50 toward a front thereof. Therefore, independent air circulation may be achieved in each space inside of the cultivation space S1 partitioned by the beds 50.

The air inside of the cultivation space S1 is circulated by the blower 80, and especially, the circulated air passes through the evaporator 31 so that the entire inside of the cultivation space S1 has a uniform temperature, and the cultivation space S1 may be able to quickly adjust the temperature. In addition, the air circulated by the blower 80 may flow while passing an upper surface of the bed 50 and a lower surface of the light emitting portion 70. The air blown by the blower 80 facilitates the breathing of plants grown in the cultivation portion 60 seated on the bed 50 while passing along the upper surface of the bed 50, and the plant may be shaken, and thus, stress of the plant may be adjusted and optimal airflow necessary for growth may be provided.

The air blown by the blower 80 may prevent overheating of the light emitting portion 70 while passing along the lower surface of the light emitting portion 70. In other words, the blower 80 may be provided at a lower end of the light emitting portion 70 and an upper side adjacent to the bed 50.

The blower 80 may discharge the air heated or cooled by the heater 102 or the evaporator 31 from the upper end. The air may be suctioned at a position adjacent to the upper surface of the bed 50, and thus, the air inside of the cultivation space S1 may be circulated.

The heater 102 and the evaporator 31 may be disposed between upper and lower portions of the inner rear plate 146. At least a portion of the heater 102 and the evaporator 31 may be configured to overlap a portion of the blower 80 disposed above and below. Thus, the air heated and cooled by the heater 102 and the evaporator 31 may be circulated by the blower 80. The entire partitioned space inside of the cultivation space S1 may be evenly cooled or heated through a single heater 102 and an evaporator 31.

The blower 80 may be spaced apart from the inner rear plate 146 to facilitate inflow of cooled or heated air and may be configured so as not to interfere with the evaporator 31. In addition, the blower 80 may be configured such that an upper end thereof is coupled to a portion of a rear portion of the light emitting portion 70. In a state in which the blower 80 is mounted inside of the cultivation space S1, components included in the inner rear plate 146, including the evaporator 31, are shielded to prevent exposure to the outside.

An outlet 171 of the supply duct (not illustrated) may be provided at a bottom of the inner rear plate 146, more specifically, at a bottom of the blower 80 disposed below. The supply duct 17 may be in communication with the machine room 12, and supply carbon dioxide to the inside of the cultivation space S1 through communication hole 819 provided in the lower cabinet 19 or discharge air in the cultivation space S1 to the communication hole 819.

Figure 6A:
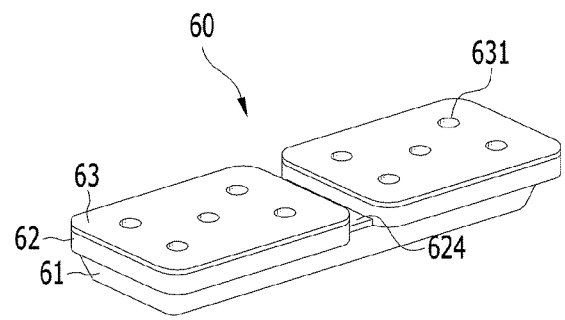
FIGS. 6A-6B illustrate, respectively, a perspective view and an exploded view illustrating a cultivation portion in a plant cultivation apparatus according to an embodiment.
Figure 6B:
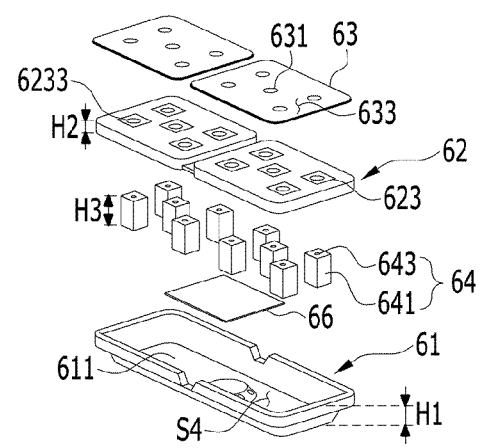

FIGS. 6A-6B illustrate, respectively, a perspective view and an exploded view illustrating a cultivation portion in a plant cultivation apparatus according to an embodiment.

FIG. 6A is a perspective view illustrating the cultivation portion in the plant cultivation apparatus according to an embodiment, and FIG. 6B is an exploded view illustrating the cultivation portion in the plant cultivation apparatus according to an embodiment.

The cultivation portion 60 may include a cultivation container 61 seated on the bed 50 and provided with an open top, and a cover portion 62 for shielding the open top of the cultivation container 61.

The cultivation container 61 is provided with an open top, and may have a size and shape corresponding to a bed seating portion 521 illustrated in FIG. 5 provided on the upper surface of the bed 50 to be seated on the bed 50.

The cultivation container 61 may have a size set to be accommodated in the bed seating portion 521. Therefore, the user may select the cultivation portion 60 of the plant desired to be cultivated, place the cultivation portion 60 in a desired position on the bed 50, and start cultivating the plant.

The cultivation container 61 may include a bottom surface 611, and a medium accommodation space S4 that accommodates the medium 64 may be formed therein. In addition, the cultivation container 61 may include a discharge hole 6135 through which water in a medium accommodation space S4 is discharged to the discharge flow path portion 512, and the water in the medium accommodation space S4 may be introduced from the water supply portion 40 through the discharge hole 6135 or may be recovered to the water supply portion 40. In addition, the discharge hole 6135 may be provided on the bottom surface 611 of the cultivation container 61 to communicate with the discharge flow path portion 512 provided in the bed 50.

The cultivation portion 60 may include a cultivation filter portion (cultivation filter) 66 provided on the bottom surface 611 of the cultivation container 61 to remove foreign matter from water discharged or introduced into the discharge hole 6135. The foreign matter removed from the cultivation filter portion 66 may be a portion of the medium 64 generated during a growth process of the plant or a portion of the root of the plant. In addition, the cultivation filter portion 66 may be configured to shield the discharge hole 6135, and foreign matter that may be generated in the medium accommodation space S4 may be prevented from being introduced into the water supply portion 40.

The cultivation container 61 may contain medium 64 in which at least a portion of the plant is embedded. In addition, the medium 64 may be provided in the medium accommodation space S4 formed by the cultivation container 61, and may extend to a predetermined height H3 from the bottom surface 611 of the cultivation container 61 toward the cover portion 62. The medium 64 may contain nutrients necessary for plant growth, and may be configured so that plant growth proceeds at an appropriate rate when only water is supplied even without a separate supply of additional nutrients.

In addition, the medium 64 may include a medium body 641 forming the outer appearance of the medium 64 and a medium hole 643 provided on an upper end surface of the medium body 641 and in which plant seeds are embedded. The medium 64 may be formed of various materials capable of absorbing water in order to supply water to seeds or roots inside of the medium 64 by absorbing water stored in the medium accommodation space S4.

The cover portion 62 may be configured to shield the medium accommodation space S4 of the cultivation container 61. As the upper portion of the cultivation container 61 is open, the cover portion 62 may be provided on the upper portion of the cultivation container 61 and coupled with the cultivation container 61.

As the water supplied to the medium 64 may be stored in the medium accommodation space S4, when exposed to the air outside of the cultivation portion and the light irradiated by the light emitting portion 70, propagation of microorganisms may be active in the water, which adversely affects the growth of the plant. To prevent this, the cover portion 62 is configured to shield the medium accommodation space S4 of the cultivation container 61, preventing the medium accommodation space S2 from being exposed to the outside of the cultivation portion 60.

Due to the cover portion 62, the water stored in the medium accommodation space S4 may be prevented from being exposed to light irradiated by the light emitting portion 70 provided on the upper portion of the cultivation portion 60, and thus, it may be prevented from coming into contact with air outside of the cultivation portion 60. In addition, due to the cover portion 62, the roots of the plant growing in the medium 64 are prevented from being exposed to the light emitting portion 70, so that the growth of the plant may be improved.

The cover portion 62 may be combined with the cultivation container 61 in a bolt-nut structure, for example; however, embodiments are not limited thereto. Hereinafter, as illustrated in the drawing, an example will be described in which the cover portion 62 is coupled to the cultivation container 61 through an interference fit.

The cover portion 62 may include a medium accommodation portion 623 provided at a position corresponding to the medium 64 and into which an upper end portion of the medium 64 is inserted. Due to the medium accommodation portion 623, when the cover portion 62 is coupled to the cultivation container 61, a position of the medium 64 inside of the cultivation container 61 may be fixed.

The cover portion 62 extends to a predetermined height H2 and may extend from a lower portion to an upper portion. The height of the medium accommodation portion 623 may be formed to accommodate the upper end portion of the medium 64 by the height H2 of the cover portion 62.

The medium 64 and the medium accommodation portion 623 may be provided as a plurality, and the medium accommodation portion 623 may be provided in a number corresponding to the number of the medium 64. In order to fix the position of the medium 64, the number of the medium accommodation portions 623 may be provided at least equal to or greater than the number of the medium 64.

As illustrated in FIG. 6(B), the medium accommodation portion 623 may be disposed at a center of an upper surface of the cover portion 62 and may be disposed as a plurality along a circumference of the cover portion 62, for example; however, embodiments are not limited thereto. A distance between the plurality of medium accommodation portions 623 may be appropriately designed according to a type of plant to be cultivated.

The medium accommodating portion 623 may include a cover through-hole 6233 that penetrates at a position corresponding to the medium 64 and exposes at least a portion of an upper end surface of the medium 64. As the medium accommodation portion 623 may be configured to be exposed on the upper surface of the cover portion 62, it may be understood that the cover through-hole 6233 also passes through an upper surface of the cover portion 62.

Seed embedded in the medium hole 643 germinates, and the stem of a plant may pass through the cover through-hole 6233 and grow toward the upper portion of the cover portion 62. Therefore, for smooth growth of the plant, a diameter of the cover through-hole 6233 may be larger than that of the medium hole 643. In other words, when viewing the cultivation portion 60 from the upper portion, the cover through-hole 6233 may be formed to expand with respect to a radial direction of the medium hole 643. The diameter of the cover through-hole 6233 may be appropriately designed considering the size of a plant to be cultivated.

In addition, the center of the cover through-hole 6233 may be configured to correspond to the center of the medium hole 643. As a result, when the plant germinates and grows and is exposed to the outside of the medium 64, recognition of the plant may not be hindered due to the cover through-hole 6233.

The cultivation portion 60 may further include a mark portion 63 provided on the upper surface of the cover portion 62 to minimize exposure of the medium 64 and on which a seed name of the plant is written. The mark portion 63 is provided to describe the seed name of the plant, so that the type of plant growing in the cultivation space S1 may be easily recognized.

The mark portion 63 may be configured to cover the upper surface of the cover portion 62. As illustrated in the drawing, the mark portion 63 is provided as a plurality and is provided on the upper surface of the cover portion 62, and may be coupled to a remaining region of the cover portion 62 except for cover coupling portion 624. Due to this, when viewing the cultivation portion 60 from the upper portion of the cultivation portion 60, upper surface 633 of the mark portion 63 is exposed, and, except for the cover coupling portion 624, the upper surface of the cover portion 62 may not be exposed.

The mark portion 63 is penetrated at a position corresponding to the cover through-hole 6233 and is provided with a cover hole 631 smaller than the diameter of the cover through-hole 6233, so that the medium 64 may be prevented from being exposed to the outside. The plant may pass through the mark hole 631 and grow toward the upper portion of the cultivation portion 60.

Figure 7A:
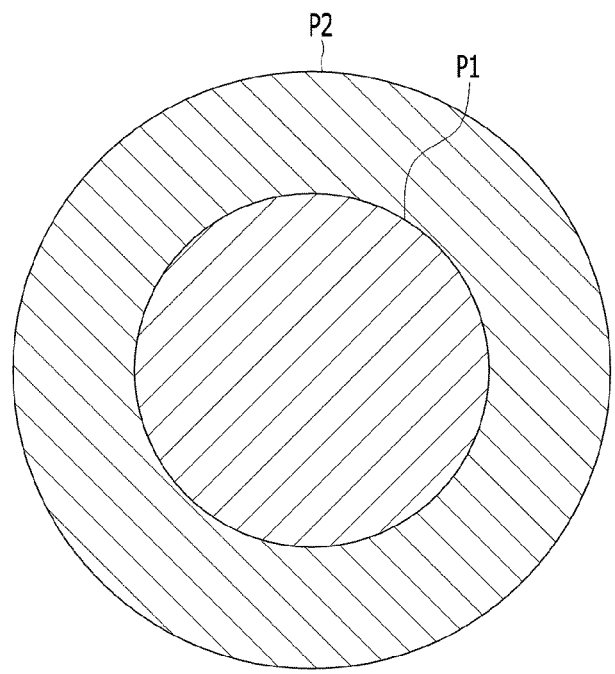
FIGS. 7A-7B are diagrams illustrating, respectively, a first region and a second region in an image photographed by a photographing portion in a plant cultivation apparatus according to an embodiment.
Figure 7B:
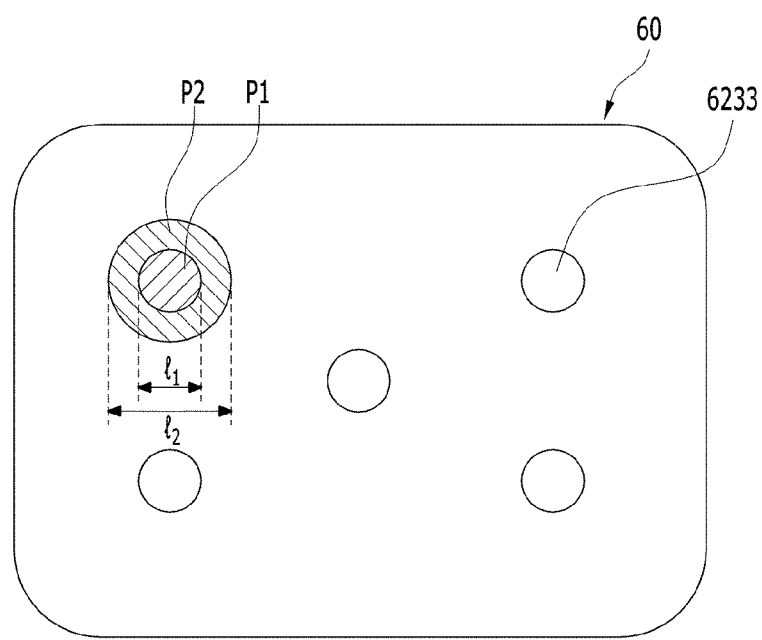

FIGS. 7A-7B are diagrams illustrating a first region and a second region in an image photographed by a photographing portion in a plant cultivation apparatus according to an embodiment. Repetitive discussion of structure has been omitted.

FIG. 7A illustrates first region P1 and second region P2 in image P photographed by the photographing portion 1100. When the photographing portion 1100 photographs the cultivation portion 60, the cultivation portion 60 may include mark portion 63 provided on the upper surface of the cover portion 62, and may include cover hole 631 in the image P. In other words, in the image P described hereinafter, a state is described in which a region of the cover through-hole 6233 may be replaced with a region of the mark hole 631 of the mark portion 63. However, for convenience of explanation, in a state is described in which the mark portion 63 of the cultivation portion 60 is omitted and the photographing portion 1100 photographs the upper surface of the cover portion 62.

In the image P, the first region P1 may include the cover through-hole 6233. The second region P2 may correspond to a region surrounding the first region. The first region P1 may not be limited to the cover through-hole 6233, and may extend from the cover through-hole 6233 in the radial direction of the cover through-hole 6233, but, hereinafter, for convenience of description, it will be described as corresponding to the region of the cover through-hole 6233.

In FIGS. 7A-7B, the first region P1 and the second region P2 are illustrated as being circles; however, embodiments are not limited thereto, and may be set as regions having various shapes of ellipses and polygons according to the size of the plants. Hereinafter, for convenience of explanation, they are described as circles.

As illustrated in FIG. 7B, diameter 11 of the first region P1 may be formed to be the same as diameter 11 of the cover through-hole 6233. Diameter 12 of the second region P2 may be larger than the diameter of the first region P1.

The diameter 12 of the second region P2 may be formed differently according to the diameter 11 of the first region P1, and the diameter 12 of the second region P2 may be differently formed according to the size of the plant and the diameter 11 of the cover through-hole 6233. The second region P2 may have a same width as the first region P1; however, embodiments are not necessarily limited thereto. The controller 90 may be configured to determine an abnormal state of the plant according to a region ratio occupied by the plant with respect to at least one of the first region P1 or the second region P2 in the image P obtained by photographing the cultivation portion 60 by the photographing portion 1100.

Figure 8A:
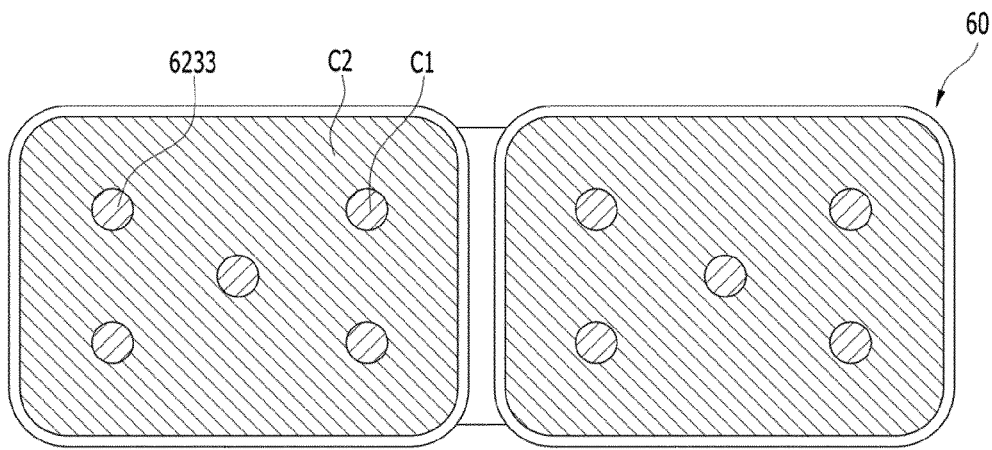
FIGS. 8A-8B are views illustrating positions of a first region and a second region on a cover portion in an image photographed by a photographing portion in a plant cultivation apparatus according to an embodiment.
Figure 8B:
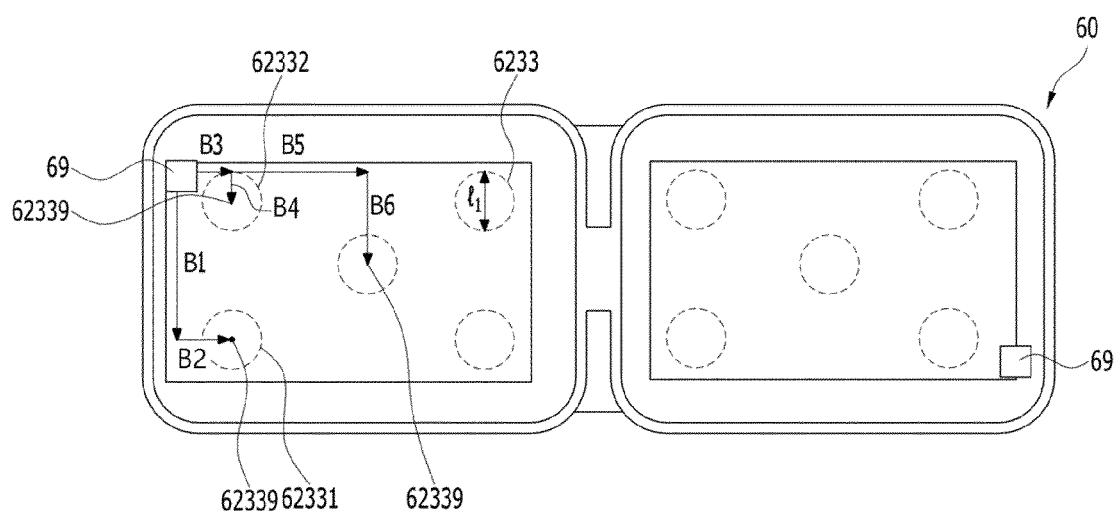

FIGS. 8A-8B are views illustrating positions of a first region and a second region on a cover portion in an image photographed by a photographing portion in a plant cultivation apparatus according to an embodiment. In the plant cultivation apparatus 1 according to an embodiment, the controller 90 may use a color difference between cover portion 62 and cover through-hole 6233 in image P to be capable of performing a first position determination mode (S110) defining the first region P1.

More specifically, the cover portion 62 and medium 64 may be provided to have different colors, and color C1 of the medium 64 exposed to the photographing portion 1100 by the cover through-hole 6233 may appear on the image P. As illustrated in FIG. 8A, in the image P, the color C1 of the cover through-hole 6233 may be the same as the color C1 of the medium 64, and a color C2 of the cover portion 62 may be provided to have a color different from the color C1.

The controller 90 may defines a position and size of the first region P1 in first position determination mode (S110) and may define the second region P2 to extend from the first region P1 in the radial direction. In other words, the controller 90 may define the second region P2 extending from the first region P1 in the radial direction by a predetermined distance from the first region P1 in the first position determination mode (S110). Although the predetermined distance is not illustrated, the predetermined distance may be stored as data in a memory portion (not illustrated) for transmitting and receiving control signals to and from the controller 90. In this way, the controller 90 may easily define the first region P1 and the second region P2 through a simple image analysis using color difference between the cover portion 62 and the cover through-hole 6233 in the image P.

As illustrated in FIG. 8B, the cover portion 62 may include a display portion (display) 69 a position of which relative to the cover through-hole 6233 is determined. Accordingly, when the photographing portion 1100 photographs the cultivation portion 60, the image P of the photographing portion 1100 may include the display portion 69.

In addition, the controller 90 may identify the position of the display portion 69 in the image P and perform a second position determination mode (S120) in which the first region P1 is defined by reflecting the relative position. More specifically, relative positions of the display portion 69 and the plurality of cover through-holes 6233 may be stored in the memory portion (not illustrated). As illustrated in FIG. 8B, any one cover through-hole 62331 of the plurality of cover through-holes 6233 may be spaced apart from the display portion 69 in second direction d2 by a separation distance B1 and in first direction d1 by a separation distance B2.

Further, another cover through-hole 62339 of the plurality of cover through-holes 6233 may be spaced apart from the display portion 69 in the second direction d2 by a separation distance B4 and in the first direction d1 by a separation distance B3. Furthermore, another cover through-hole 6233 of the plurality of cover through-holes 6233 may be spaced apart from the display portion 69 in the second direction d2 by a separation distance B6 and in the first direction d1 by a separation distance B5.

As described above, the separation distances B1, B2, B3, B4, B5, and B6 may be stored in the memory portion (not illustrated), and in the second position determination mode (S120), the controller 90 may set the location of center 62339 of the cover through-hole 6233 by receiving information on the separation distances B1, B2, B3, B4, B5, and B6 from the memory portion (not illustrated).

The controller 90 may define the first region P1 and the second region P2 through the first position determination mode (S110) or the second position determination mode (S120). In at least one of the first region P1 or the second region P2, a germination determination mode (S200) of determining whether the plant has germinated may be performed based on a region ratio occupied by the plant.

Figure 9A:
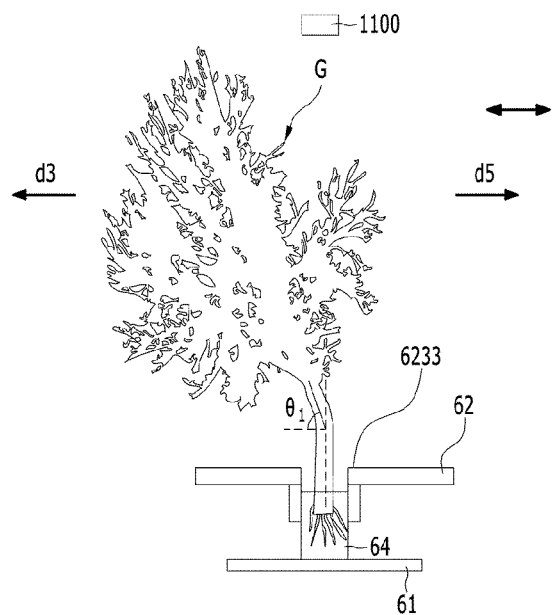
FIGS. 9A-9B illustrate, respectively, a side view illustrating a hardness state of a plant in a plant cultivation apparatus according to an embodiment and an image of a plant in a hardness state and a cultivation portion photographed by a photographing portion.
Figure 9B:
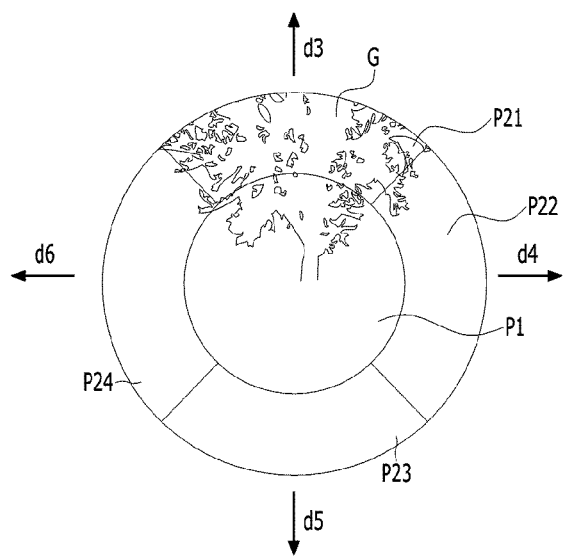

FIGS. 9A-9B illustrate, respectively, a side view illustrating a hardness state of a plant in a plant cultivation apparatus according to an embodiment and an image of a plant G in a hardness state and a cultivation portion photographed by a photographing portion. Repetitive discussion of structure has been omitted.

FIG. 9A is a side view illustrating the hardness state of the plant in the plant cultivation apparatus 1 according to an embodiment. At an early stage after germination of plant G, a stem portion of the plant is weak and cannot withstand a weight of the leaves and may grow in a state of being tilted. The controller 90 may perform a hardness determination mode (S300) for determining whether or not the plant G has fallen through a region ratio occupied by the plant G in at least one of the first region P1 or the second region P2. The plant G may be provided to have a color different from that of the cover portion 62 and the medium 64.

The plant G may grow by being inclined at a predetermined angle 61 based on an extension direction of the upper surface of the cover portion 62. The controller 90 may determine the hardness state of the plant G, based on a reference value through the region ratio occupied by the plant G in at least one of the first region P1 or the second region P2 in the hardness determination mode (S300), if the region ratio is equal to or greater than the reference value.

In addition, the controller 90 may determine as a fallen state of the plant, when the region ratio occupied by the plants G in the first region P1 is equal to or less than the first region ratio and the region ratio occupied by the plants in the second region is equal to or greater than the second region ratio. For example, the controller 90 may determine as the hardness state of the plant G, in the hardness determination mode (S300), when the region ratio occupied by the plant G in the first region P1 is lower than the first region ratio of 3%, and the region ratio occupied by the plant G in the second region P2 is higher than the second region ratio of 5%. However, the first region ratio and the second region ratio may be set differently according to the type of the plant G, and are not necessarily limited to the above values.

FIG. 9B illustrates image P obtained by photographing the plant G in the hardness state and the cultivation portion 60 by the photographing portion 1100. As illustrated, the plant G may grow inclined toward third direction d3. In addition, the second region P2 may be divided into a plurality of regions along a circumference of the first region P1, and thus, may include a 2-1 region P21, a 2-2 region P22, a 2-3 region P23, and a 2-4 region P24.

The 2-1 region P21 may be disposed in the third direction d3 based on the first region P1, and the 2-2 region P22 may be disposed in the fourth direction d4 based on the first region P1, the 2-3 region P23 may be disposed in the fifth direction d5 based on the first region P1, and the 2-4 region P24 may be disposed in the sixth direction d6 based on the first region P1. Accordingly, the controller 90 may determine the direction in which the plant has fallen by identifying the region ratio occupied by the plant in each of the plurality of regions P21, P22, P23, and P24.

For example, as illustrated in the drawing, it may be determined that the plant G is inclined in the third direction d3 by comparing the area ratio occupied by the plant in the 2-1 area P21 with those in the 2-2 area, the 2-3 area, and the 2-4 area. Of course, the second region P2 may include five or more divided regions, and in some cases, the direction in which the plant G falls may be determined as a direction between the third direction d3 and the fourth direction d4.

Figure 10:
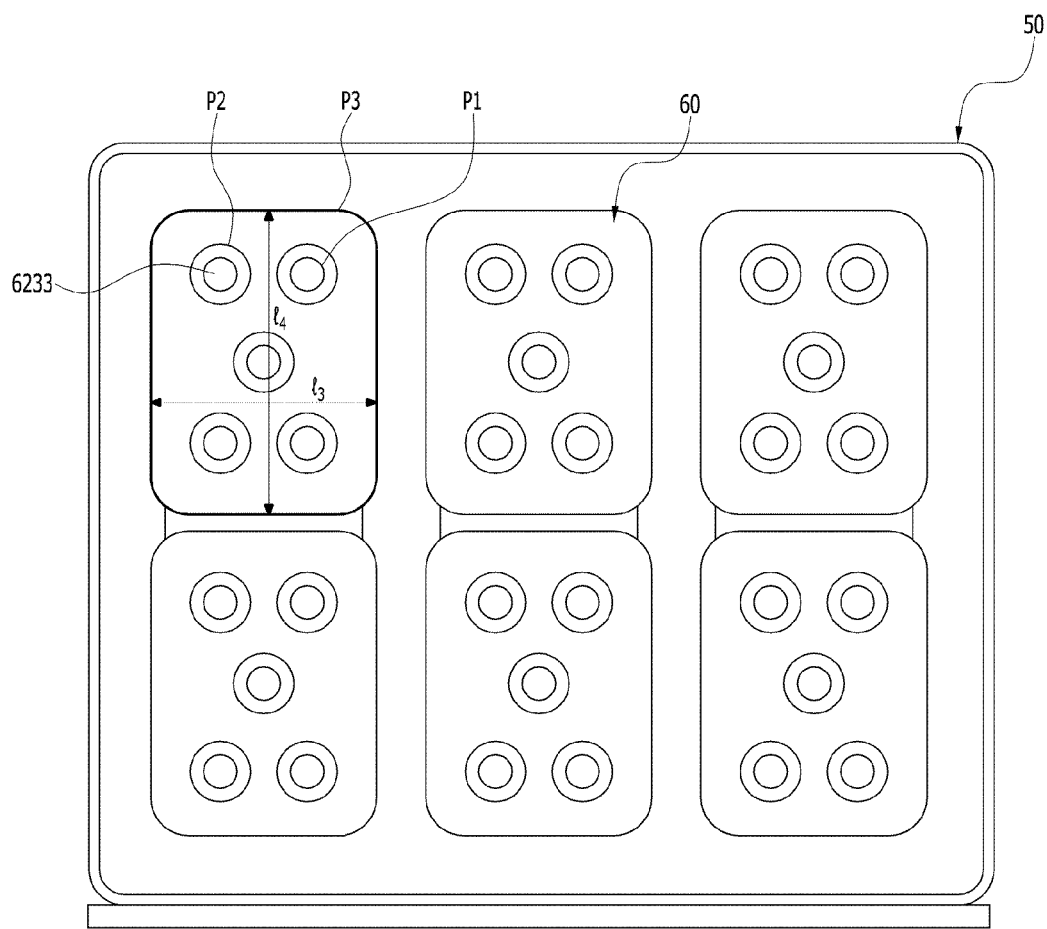
FIG. 10 is an image of a bed and a plurality of cultivation portions photographed by a photographing portion in a plant cultivation apparatus according to an embodiment.

FIG. 10 is an image of a bed and a plurality of cultivation portions photographed by a photographing portion in a plant cultivation apparatus according to an embodiment.

The controller 90 may perform a growth abnormality determination mode (S400) which determines whether plant G is in a growth abnormality state by identifying the color of the plant G in the image P of the photographing portion 1100. The image P of the photographing portion 1100 may include a third region P3 corresponding to a remaining region excluding the first region P1 and the second region P2 of the upper surface 611 of the cover portion 62. The controller 90 may determine as a growth abnormality state of the plant when the growth abnormality color from the plant G is identified in the second region P2 and the third region P3 in the growth abnormality determination mode (S400).

As illustrated, the third region P3 may form a distance 14 of the cover portion 62 extending along the first direction d1 and a distance 13 of the cover portion 62 extending along the second direction d2 horizontally and vertically. The color of the plant in the abnormal state may be different from the color of the plant in a normal state. For example, the controller 90 may set the color of the plant in the normal state to green, and may set the color of the plant in the abnormal state to yellow or brown.

In the growth abnormality determination step (S400), the controller 90 may determine that the plant is in an abnormal state when the color of the abnormal state of the plant determined in the second region and the third region P3 exceeds a reference value, for example, 3%.

The abnormal state may correspond to tip burn, or old leaf, for example. The color of the abnormal state may be expressed in the leaf of the plant.

Figure 11A:
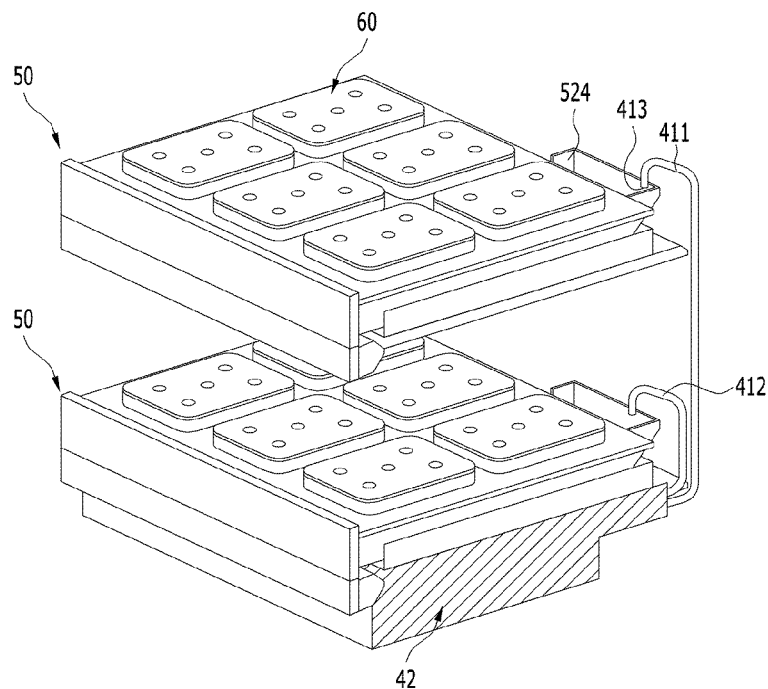
FIGS. 11A-11B illustrate, respectively, a perspective view and a side view illustrating a water supply portion in a plant cultivation apparatus according to an embodiment.
Figure 11B:
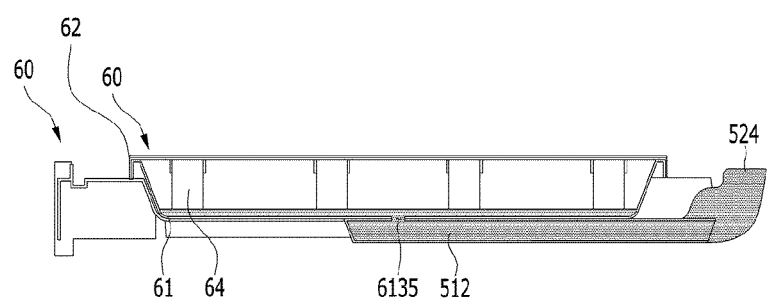

FIGS. 11A-11B are perspective views illustrating a state in which the bed and the cultivation portion are seated in the plant cultivation apparatus according to an embodiment. Repetitive discussion of structure has been omitted.

The water supply portion 40 may include a water supply portion 40 that supplies water to the cultivation portion 60 and a storage portion (not illustrated) that supplies, recovers, and stores water necessary for the cultivation portion 60. First water supply flow path portion 411 and second water supply flow path portion 412 are disposed independently and extend toward the cultivation portion 60 to supply water necessary for plant growth.

The first water supply flow path portion 411 may be connected to the storage portion (not illustrated) and then extend to an upper portion so that water is introduced from the storage portion (not illustrated) and moved to the bed water collection portion 524 of the upper bed 50. The second water supply flow path portion 412 may be connected to the storage portion (not illustrated) and then extend to the upper portion such that water is introduced from the storage portion (not illustrated) and moved to the bed water collection portion 524 of the lower bed 50. Accordingly, the water supply portion 40 may be configured to supply water to the upper bed 50 and the lower bed 50, respectively.

The water supply portion 40 may have a discharge hole 413 provided at a position corresponding to the bed water collection portion 524. Water supplied from the first water supply flow path portion 411 and the second water supply flow path portion 412 may be directly introduced into the bed water collection portion 524.

The water supply portion 40 may be formed of a metal pipe, such as stainless steel. Therefore, the water supply portion 40 may be hygienically managed and may maintain its shape firmly, thereby preventing the flow path from becoming clogged due to deformation or bending, and improving reliability of water supply.

The structure in which water is supplied to the upper bed 50 and the lower bed 50 is the same with only a difference in upper and lower positions. The water supplied to the bed water collection portion 524 may supply moisture to the cultivation portion 60 which is mounted on the bed 50. In addition, the first water supply flow path portion 411 and the second water supply flow path portion 412 are disposed independently and extend toward the cultivation portion 60 so as to supply water necessary for plant growth.

The water supply case 42 may be provided under the bed 50 and coupled to the cabinet 10. Due to the water supply case 42, the storage portion (not illustrated), a supply pump portion (not illustrated), a flow rate sensor (not illustrated), and a branch valve (not illustrated) are not exposed to the outside, so that reliability of the water supply portion 40 may be improved, and an outer appearance may be neatly formed.

The water supply portion 40 may include the storage portion (not illustrated) in which water supplied to the plant is stored, and the supply pump portion (not illustrated) configured to pressurize the water in the storage portion (not illustrated) to the water supply portion 40. The water supply portion 40 may include the water supply case 42, components located inside of the water supply case 42, and pipes connected to these components.

In addition, the flow rate sensor (not illustrated) senses a flow rate of the supplied water, and may prevent overflow due to excessive supply of water to the cultivation portion 60. The amount of water supplied to the cultivation portion 60 may be adjusted by supplying metered water through the flow rate sensor (not illustrated).

Therefore, it is possible to supply an optimal amount of water to the cultivation portion 60 for each growth stage of the plant so as not to maintain a state in which excessive moisture is stored in the cultivation portion 60. Through this, it is possible to maintain the cultivation portion 60 clean at all times, and to properly maintain the humidity in the bed 50 and the cultivation space S1. In other words, water in the storage portion (not illustrated) may be supplied to the cultivation portion 60 or the bed 50 by passing through the branch valve (not illustrated) by the operation of the supply pump portion (not illustrated).

Figure 12:
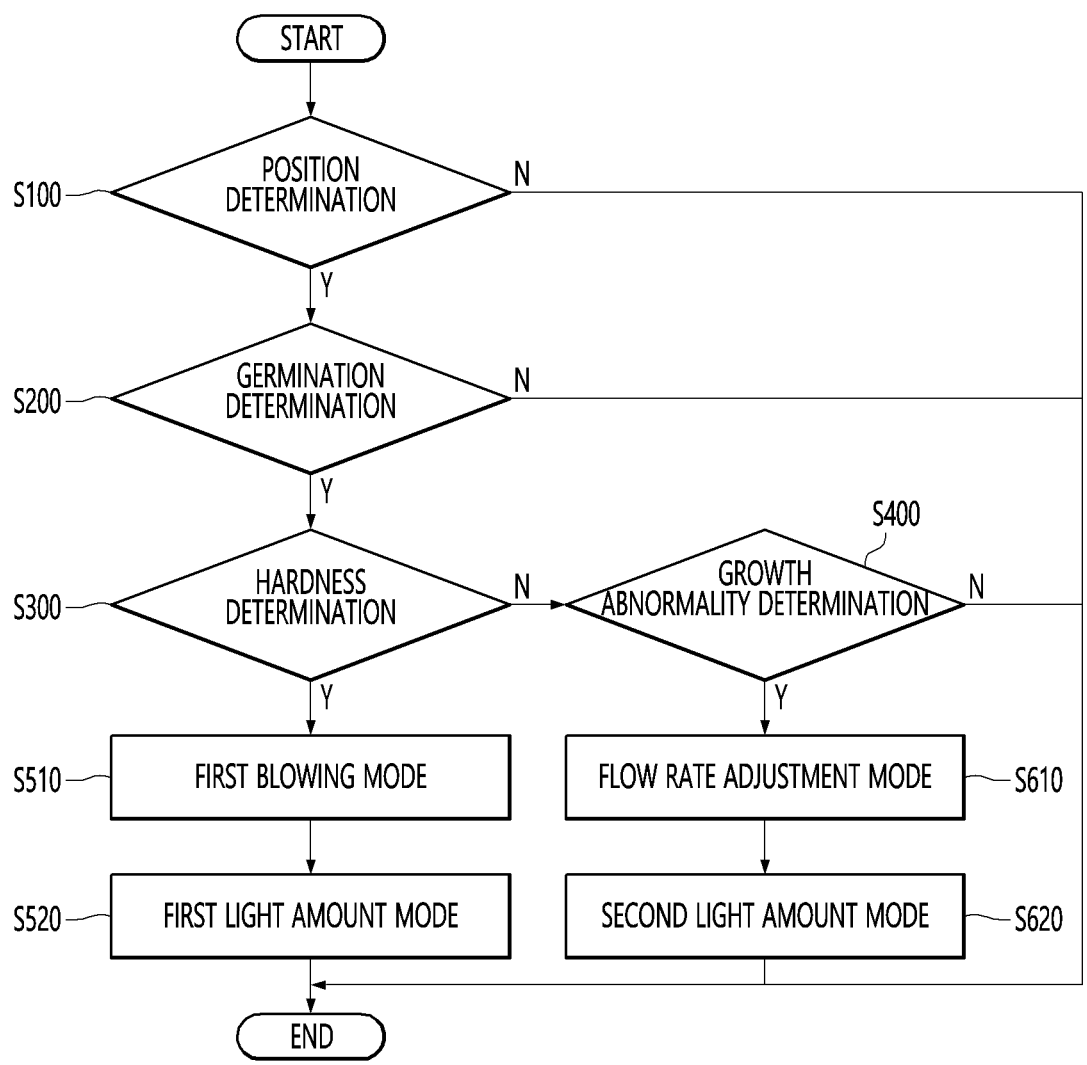
FIG. 12 is a diagram illustrating various embodiments of an adjustment mode performed by a control portion in a plant cultivation apparatus according to an embodiment.

FIG. 12 is a diagram illustrating various embodiments of a control mode performed by the controller in the plant cultivation apparatus according to an embodiment. Repetitive discussion of structure has been omitted.

The controller 90 may perform a position determination (S100) of determining locations of first region P1 and second region P2 in image P. As described above, cultivation portion 60 may be separated from bed 50, and in this case, even if photographing portion 1100 photographs the upper surface of bed 50, in the image P, the cultivation portion 60 may not be included. The controller 90 cannot determine the positions of the first region P1 and the second region P2 in the image P, and the control may end.

On the other hand, as described above, the position determination (S100) may include first position determination (S110) and second position determination (S120), and the controller 90 may perform germination determination (S200) when defining the first region P1 and the second region P2. The controller 90 may determine whether the plant has germinated through a region ratio occupied by the plant in at least one of the first region P1 or the second region P2 in the germination determination (S200). If the region ratio occupied by the plant in at least one of the first region P1 or the second region P2 is equal to or greater than the reference value of 5%, it may be determined that the plant has germinated. In addition, the reference value of 5% may be set differently depending on the type of the plant.

If the controller 90 determines that the plant has not germinated in the germination determination (S200), the control operation may end.

On the other hand, as described above, if it is determined that the plant has germinated in the germination determination (S200), a hardness determination (S300) of determining whether the plant has fallen may be performed. When it is determined in the hardness determination (S300) that the plant is inclined more than the reference value, the controller 90 may control the blower 80 to perform a blowing mode for adjusting the amount of air circulation in the cultivation space S1.

The blowing mode may include first blowing mode (S510), and the controller 90 may induce resolution of the falling of the plant by further reducing a rotational speed of blower fan 82 than the basic rotational speed of the blower fan 82 before starting the control in the first blowing mode (S510).

In addition, when it is determined that the plant is tilted more than a reference value in the hardness determination (S300), the controller 90 controls the light emitting portion 70 to increase the amount of light of light emitting body 72, so that the controller 90 may perform a first light amount adjustment mode (S520) for inducing recovery of the plant in the fallen state. The first blowing mode (S510) may be performed simultaneously with the first light amount adjustment mode (S520), and the order of performing the first blowing mode (S510) and the first light amount adjustment mode (S520) may vary.

The growth abnormality determination (S400) may be executed after the hardness determination (S300) is performed, or may be performed before the hardness determination (S300). When the growth abnormality state of the plant is determined in the growth abnormality determination (S400), the controller 90 controls the light emitting portion 70 to make the light amount of the light emitting body 72 lower than the basic light amount before performing the growth abnormality determination (S400), and thus, may perform a second light amount adjustment mode (S620) for inducing recovery of the plant in the growth abnormality state.

In addition, when it is determined that the plant is in the growth abnormality state in the growth abnormality determination (S400), the controller 90 controls the water supply portion 40, and thus, may perform a flow rate adjustment mode (S610) for adjusting nutrient solution supplied to the cultivation portion 60. Nutrient solution may be adjusted by adjusting the supply pump portion of the water supply portion 40.

In addition, the flow rate adjustment mode (S610) may be performed simultaneously with the second light amount adjustment mode (S620), and the order of execution of the flow rate adjustment mode (S610) and the second light amount adjustment mode (S620) may vary. The first light amount adjustment mode (S520) and the second light amount adjustment mode (S620) may be individually performed by the plurality of light emitting portions 70.

In addition, the display portion 1000 may be configured to display germination status, growth abnormality, and hardness status of plants from the controller 90.

In addition, the blowing mode may include a second blowing mode, and the controller 90 may be configured to stop operation of the blower fan 82 in the second blowing mode, and thus, to increase the quality of the image P photographed by the photographing portion 1100.

In addition, the light amount adjustment mode may include a third light amount adjustment mode, and the controller 90 may be configured to stop operation of the light emitting body 72 in the third light amount adjustment mode, and thus, increase the quality of the image P photographed by the photographing portion 1100.

Although various embodiments have been described, those skilled in the art may make various modifications to the various embodiments described above without departing from the scope. The scope should not be limited to the various embodiments described and should not be defined thereto, and should be defined by the claims to be described and those equivalent to the claims.

The invention claimed is:

1. A plant cultivation apparatus, comprising:
a cabinet;
at least one bed provided inside of the cabinet;
a cultivation portion provided on the at least one bed;
a medium accommodated in the cultivation portion and in which at least a portion of a plant is embedded;
a camera provided in the cabinet and configured to create an image by photographing the cultivation portion; and
a controller configured to receive the image created by the camera, wherein the cultivation portion includes:
a cultivation container seated on the at least one bed, having an open top, and configured to accommodate the medium therein; and
a cover configured to shield the open top of the cultivation container and having at least one cover through-hole formed at a position corresponding to the medium, wherein the image from the camera includes a first region including the at least one cover through-hole and a second region surrounding the first region and positioned inside of the cover through-hole, and wherein the controller is configured to determine an abnormal state of the plant according to a region ratio occupied by the plant in at least one of the first region or the second region.

2. The plant cultivation apparatus of claim 1, wherein the controller is configured to perform a first position determination mode for defining the first region using a color difference between the cover portion and the at least one cover through-hole in the image.

3. The plant cultivation apparatus of claim 2, wherein the controller is configured to define the second region extending in a radial direction from the first region by a predetermined distance in the first position determination mode.

4. The plant cultivation apparatus of claim 1, wherein the cover portion includes a display provided to determine a position of the at least one cover through-hole by using a preset relative position with respect to the at least one cover through-hole, wherein the image of the camera includes the display, and wherein the controller is configured to perform a second position determination mode for defining the first region by identifying a position of the display in the image and reflecting the relative position.

5. The plant cultivation apparatus of claim 1, wherein the controller is configured to perform a germination determination mode for determining whether the plant has germinated based on the region ratio occupied by the plant in at least one of the first region or the second region.

6. The plant cultivation apparatus of claim 5, wherein the controller identifies the region ratio occupied by the plant in at least one of the first region or the second region through a color difference between the cover portion, the at least one cover through-hole, and the plant identified in the image in the germination determination mode.

7. The plant cultivation apparatus of claim 1, wherein the controller is configured to perform a hardness determination mode for determining whether the plant has fallen through the region ratio occupied by the plant in at least one of the first region or the second region.

8. The plant cultivation apparatus of claim 7, wherein the controller is configured to determine that the plant is in a fallen state when the region ratio occupied by the plant in the first region is equal to or less than 3% and the region ratio occupied by the plant in the second region is equal to or greater than 5%.

9. The plant cultivation apparatus of claim 8, wherein the second region is divided into a plurality of zones along a circumference of the first region, and wherein the controller is configured to determine a falling direction of the plant by identifying a region ratio occupied by the plant for each of the plurality of zones.

10. The plant cultivation apparatus of claim 7, wherein a cultivation space in which the plant is cultivated is formed inside of the cabinet, wherein the plant cultivation apparatus further comprises a blower including a blower fan provided in the cabinet to circulate air in the cultivation space, and wherein the controller is configured to perform a plurality of blowing modes for adjusting an amount of air circulation in the cultivation space by controlling the blower when the fallen state of the plant is determined in the hardness determination mode.

11. The plant cultivation apparatus of claim 10, wherein the controller is configured to perform a first blowing mode in which a rotational speed of the blower fan is reduced to prevent falling of the plant.

12. The plant cultivation apparatus of claim 11, wherein the controller is configured to perform a second blowing mode in which an operation of the blower fan is stopped to increase a quality of the image photographed by the camera.

13. The plant cultivation apparatus of claim 7, further comprising:
a light emitting portion including a light emitting body provided inside of the cabinet and that irradiates light toward the cultivation portion, wherein when the controller determines that the plant is in the fallen state in the hardness determination mode, the controller controls the light emitting portion to increase a light amount of the light emitting body so that a light amount adjustment mode for inducing recovery of the plant in the fallen state is performed.

14. The plant cultivation apparatus of claim 1, wherein the controller is configured to perform a growth abnormality determination mode for determining whether the plant is in a growth abnormality state by identifying a color of the plant in the image of the camera.

15. The plant cultivation apparatus of claim 14, wherein the image of the camera includes a third region corresponding to a region other than the first region and the second region of an upper surface of the cover portion, and wherein the controller is configured to determine that the plant is in a growth abnormality state when the color is identified from the plant in the second region and the third region in the growth abnormality determination mode.

16. The plant cultivation apparatus of claim 14, further comprising:
a light emitting portion including a light emitting body provided inside of the cabinet and that irradiates light toward the cultivation portion, wherein when the plant is determined to be in the growth abnormality state in the growth abnormality determination mode, the controller controls the light emitting portion to reduce a light amount of the light emitting body so that a light amount adjustment mode inducing recovery of the plant in the growth abnormality state is performed.

17. The plant cultivation apparatus of claim 14, further comprising:
a water supply portion provided inside of the cabinet and configured to supply a nutrient solution to the cultivation portion, wherein the controller performs a flow rate adjustment mode for adjusting the nutrient solution supplied to the cultivation portion by controlling the water supply portion when the controller determines that the plant is in the growth abnormality state in the growth abnormality determination mode.

18. A plant cultivation apparatus, comprising:
a cabinet;
at least one bed provided inside of the cabinet;
a cultivation portion provided on the at least one bed;
a medium accommodated in the cultivation portion and in which at least a portion of a plant is embedded;
a camera provided in the cabinet and configured to create an image by photographing the cultivation portion; and
a controller configured to receive the image created by the camera and determine a status of the plant based on the photograph, wherein the cultivation portion includes:
a cultivation container seated on the at least one bed, having an open top, and configured to accommodate the medium therein; and
a cover configured to shield the open top of the cultivation container and having at least one cover through-hole formed at a position corresponding to the medium, wherein the image from the camera includes a first region including the at least one cover through-hole and a second region surrounding the first region and positioned inside the cover through-hole, and wherein the controller is configured to determine a status of the plant according to a region ratio occupied by the plant in at least one of the first region or the second region.

19. The plant cultivation apparatus of claim 18, wherein the controller is configured to determine the status of the plant using a color difference in the image between the cover, the at least one cover through-hole, and the plant.

20. The plant cultivation apparatus of claim 18, wherein the plant cultivation apparatus further comprises a light source and a blower, and wherein the controller is configured to control the light source and/or the blower based on the status of the plant.

* * * * *